(12) United States Patent
Jentzen

(10) Patent No.: US 6,224,588 B1
(45) Date of Patent: May 1, 2001

(54) FLEXIBLE FINGER LATCHING MECHANISM

(75) Inventor: S. William Jentzen, Cedar Creek, TX (US)

(73) Assignee: Saf-T-Med, Franklin Lakes, NY (US)

( * ) Notice: Subject to any disclaimer, the term of this patent is extended or adjusted under 35 U.S.C. 154(b) by 0 days.

(21) Appl. No.: 09/305,243

(22) Filed: May 4, 1999

(51) Int. Cl.[7] .................................................. A61M 5/00
(52) U.S. Cl. ............................................. 604/533; 604/241
(58) Field of Search ................................... 604/533, 523, 604/240, 241

(56) References Cited

U.S. PATENT DOCUMENTS

| 3,507,279 | 4/1970 | Senkowski | 128/221 |
| 4,770,308 | 9/1988 | Lynn | 215/330 |

FOREIGN PATENT DOCUMENTS

| 0 158 030 A1 | 2/1985 | (EP) . |
| 0 845 274 A2 | 11/1997 | (EP) . |
| 0 864 504 A1 | 2/1998 | (EP) . |

Primary Examiner—John Yasko
(74) Attorney, Agent, or Firm—Beirne, Maynard & Parsons, L.L.P.

(57) ABSTRACT

A mechanical latching device is provided for threaded connections, such as those found in a medical syringe. The connections each have a thread profile with crest and root elements. At least one flexible finger or projection extends outwardly from within one of the root portions and an outwardly extending ridge is provided on the second threaded member extending from the ridge. Interference with normal threading movements between connection elements is abated, while resistance is provided to unthreading manipulations of the connections.

4 Claims, 5 Drawing Sheets

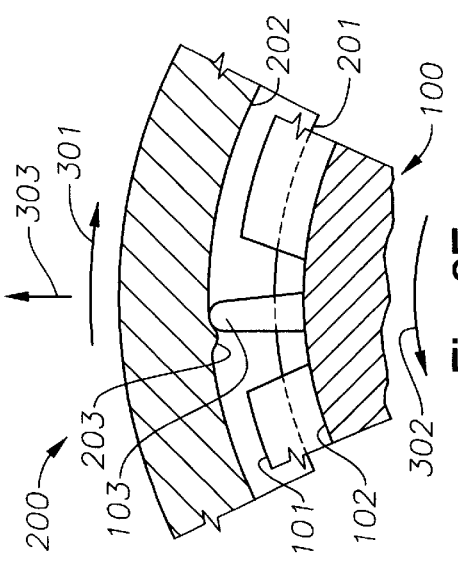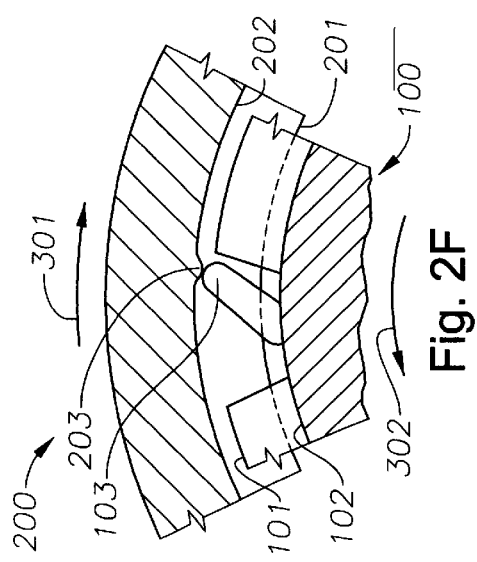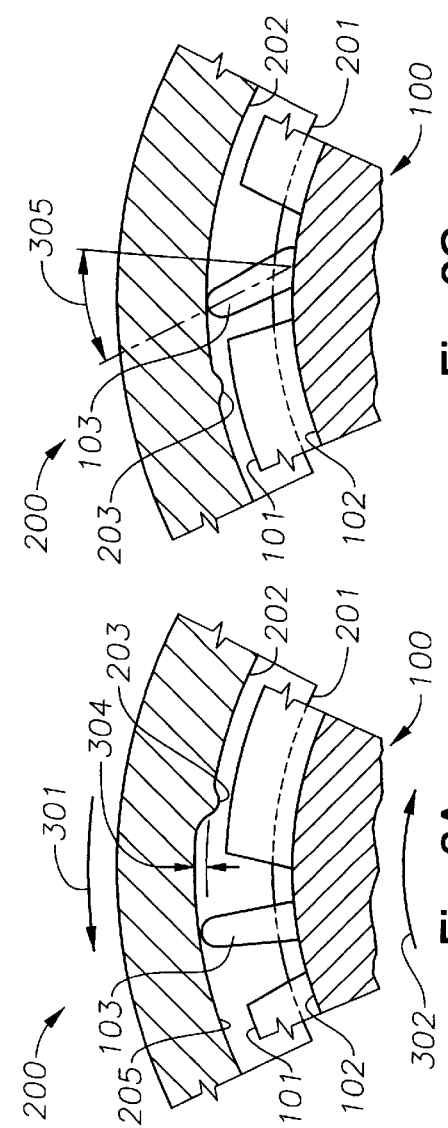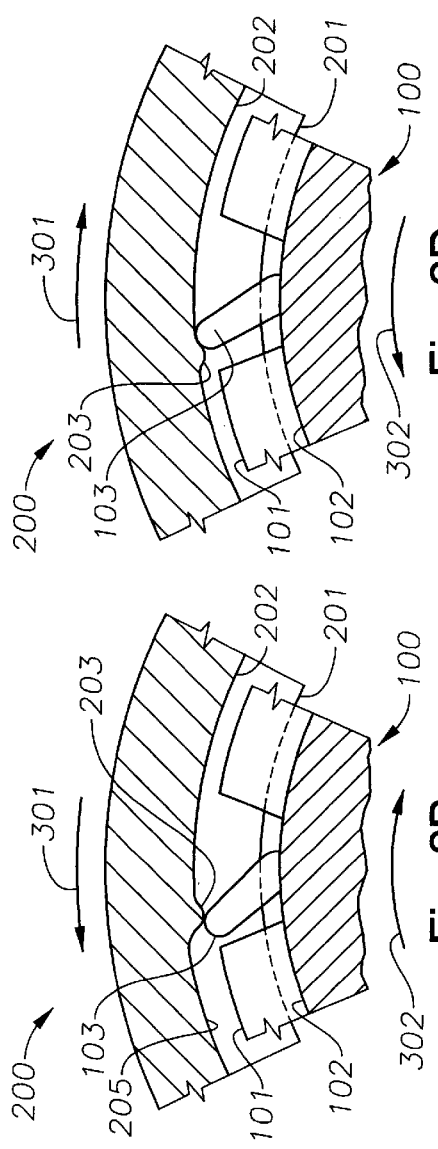
Fig. 2A (Initial Assembly)
Fig. 2B (Tightening)
Fig. 2C (Tight)
Fig. 2D (Disassembly)
Fig. 2E (Toggling Over)
Fig. 2F (Disassembly)

(Disassembled)

FLEXIBLE FINGER LATCHING MECHANISM

BACKGROUND OF THE INVENTION (1) Field of the Invention

The invention pertains to a mechanical latching device for threaded connections and to a syringe including such latching device.

(2) Brief Description of the Prior Art

A number of connections utilize threaded components, including nuts and bolts, threaded pipes and couplings, soda bottles and caps, medical connectors, syringes, and the like. Such connections are simple to mate and can be attached and disconnection many times. This simplicity comes with two side effects which are undesirable in certain applications.

First, the presence of angled threads creates the possibility of the connection self-loosening under axial loading—a term referred to as "backdriving." The greater the angle or "pitch" of the threads, the more likely that axial loading will cause backdriving. In some cases, users can add additional components such as lockwashers to prevent backdriving. In other cases, such additions are impractical or too expensive. Hence a need exists to provide backdriving resistance as an integral feature of the threaded connector.

Secondly, very little torque is often required to disassemble the connections. This can be a problem when childproofing is desired, or when one wants to discourage tampering with an assembly.

The present invention addresses such problems associated with the prior art.

An added advantage of the present invention is that it does not interfere with the ordinary function of threaded connections, and requires both mating sides to incorporate the described changes to operate. Components can be manufactured incorporating the feature, and only when assembled with a mating component also incorporating the feature would the user obtain the desired benefit. Hence a bolt with the features on the threads could still use a regular nut with no noticeable impact; a nut with the feature on its threads could use a regular bolt with no noticeable impact; but a nut and bolt combined, with the mating features described herein, would demonstrate the desired characteristics.

BRIEF DESCRIPTION OF THE DRAWINGS

FIG. 2A is a partial, sectional view of the device in FIG. 1, taken along the line A—A of FIG. 1. It shows a close up of the features prior to assembly.

FIG. 2B is the same partial, section view of FIG. 2A except the connection is beginning to be tightened to bring the device of the present invention into operation.

FIG. 2C is the same partial, section view of FIG. 2B except the connection is now tight and will resist unscrewing.

FIG. 2D is the same partial, sectional view of FIG. 2C except that the feature is shown resisting unscrewing forces.

FIG. 2E is the same partial, sectional view of FIG. 2D except the strength of resistance is beginning to be overcome.

FIG. 2F is the same partial, sectional view of FIG. 2E except the feature of the present invention is continuing to be overcome.

SUMMARY OF THE INVENTION

Figure 1:
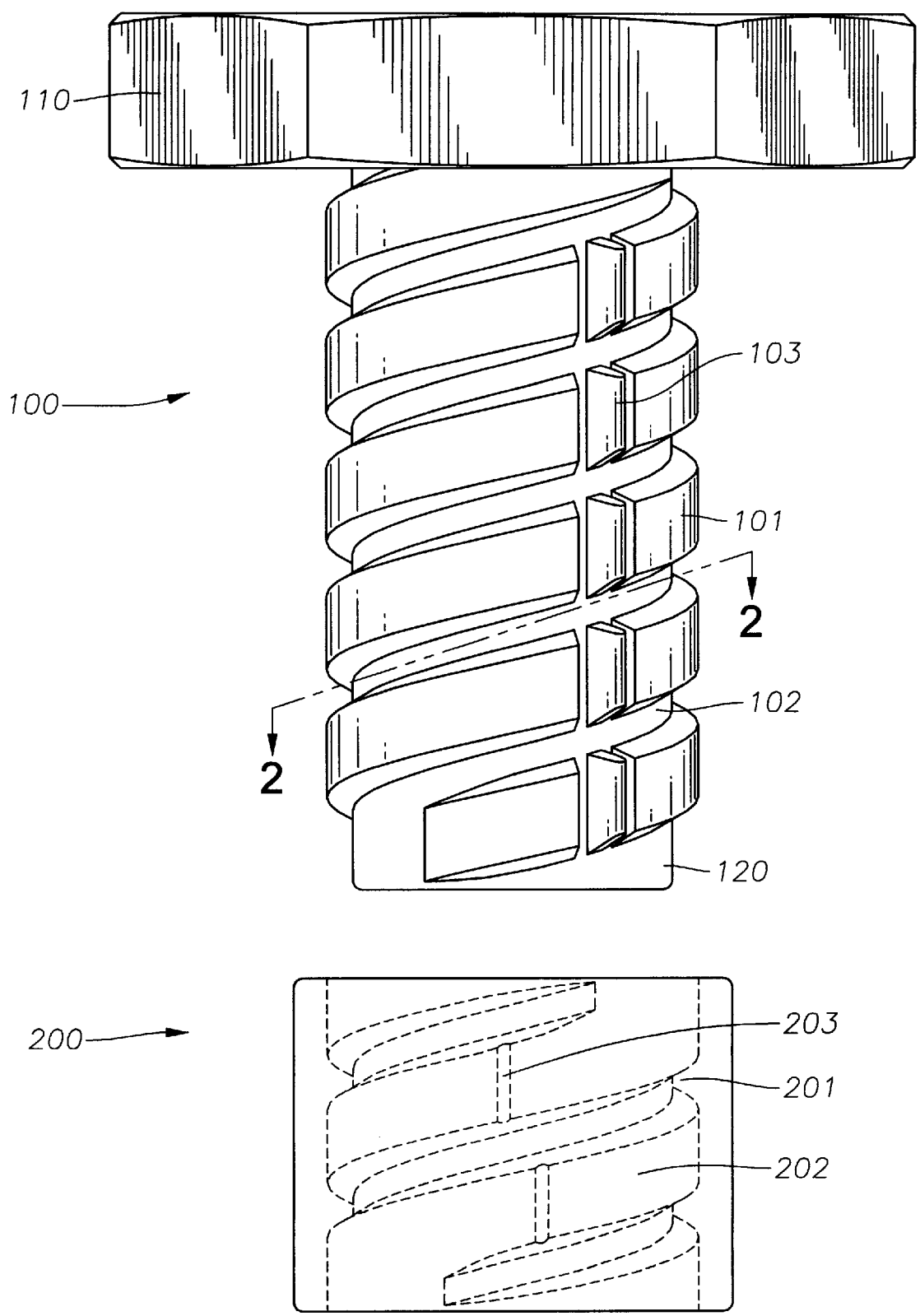
FIG. 1 is a view of the device of the present invention incorporated on a threaded bolt and nut.

The invention provides a mechanical latching device for threaded connections. A first connecting member, such as a hub in a syringe device securing a needle and a syringe barrel for interengagements with the hub, or a bolt for threaded securement with a companion nut, has an exterior threaded profile which includes first crest and root portions. The second connecting member, such as the barrel in the hub/barrel syringe arrangement, or the nut in a bolt/nut combination, is provided for mating engagement with the other member and has an interior thread profile thereon including second crest and root portions. At least one flexible finger extends outwardly within the first and second root portions. The finger has a distal end normally projecting outwardly away from one of the first and second crests, such that it is a radial axial enlargement of such crest. At least one outwardly extending ridge portion is provided on the other of the connecting members with the ridge portion forming a part of the root of the thread profile of that respective connecting member. During thread interengagement movements of the connecting members, the finger element is flexed in one direction by the ridge portion and during disengagement movements of the members, the finger is flexed in the opposite direction by the ridge for resistance to the disengagement movements.

In a preferred embodiment, the latching device is provided in a syringe for introduction or withdrawal of a liquid from a body. The syringe comprises a hollow needle for penetrating the body and a hub for receiving the needle. A syringe barrel is selectively engageable to the hub for receipt of the liquid. Thread profiles are provided on each of the hub and barrel members and include the finger or flexible projection means and the ridge portion or abutment means, as above described.

The incorporation of the threaded connection and the mechanical latching device of the present invention does not interfere with the ordinary function of threaded connections. The components of the device, such as a bolt and screw combination, or hub and barrel or other housing components of a syringe can be manufactured incorporating the latching device, and only when assembled with a mating component also incorporating the features of the latching device would the user obtain the desired benefit. Hence, a bolt with the features on the threads could still use a regular nut with no noticeable impact and a nut with the features on its threads could use a regular bolt with no noticeable impact. On the other hand, a nut and bolt combined, with the mating features of the present invention, would demonstrate the desired characteristics to be achieved by incorporation of the present invention therein.

The present invention provides features on both portions of a threaded connector to create an interference mechanism, leading to a "ratchet" effect. The extent of this interference can be pre-determined in design to provide the degree of backdriving or unscrewing resistance desired for a given application. At modest levels of resistance the feature is not damaged by repeated assembly and disassembly. At high levels of resistance the features become permanently damaged and thereby may be used to indicate tampering.

The locations of these features can be selected so that they become engaged as assembly is started, only upon completion of assembly, or throughout the entire mating process. If the feature is engaged only at that start of assembly, one has, for instance, a nut which may be freely positioned anywhere along the length of a bolt, but resists having the nut fall all the way off the end of the bolt. If the feature is engaged only at the end of the assembly, it can be used to "lock" the nut in place, yet, once the strength of the "lock" is overcome, the nut can be easily removed by hand. A bolt with the features along the length of the shaft would act like a ratchet, allowing the nut to be placed anywhere along its length and still require increased amounts of force to disassemble.

The amount of interference between the two components and the materials used in the interfering elements determines the amount of unscrewing resistance. It may range from being barely detectable, all the way through something which is nearly impossible to disassemble.

DESCRIPTION OF THE PREFERRED EMBODIMENTS

With first reference to FIG. 1, a preferred embodiment of the current invention is depicted using a male portion (in this case a bolt) or first connecting member 100, and a female portion (in this case a nut), or second connecting member, 200. These items may be made of any material using common techniques such as injection molding of some form of fairly rigid plastic, such as nylon. The bolt 100 is depicted with a head 110 and a shaft 120. The threads may take any form, but the outer-most portion 101 of the thread is generally referred to as the "crest," while the inner-most portion 102 is generally referred to as the "root." In this embodiment, the thread is shown interrupted along the length of the shaft with a plurality of projections 103. For the sake of this discussion, the projections will be referred to as "fingers" or "projections."

On a mating component or connecting member 200 is shown interior threads compatible with those on connecting member 100, with a crest 201 and a root 202. In this embodiment, interference with the fingers 103 will be provided by a plurality of ridges or abutments 203 located on the root segments.

While depicted as residing within the threads, it is important to note that the feature could just as easily have been incorporated in any area of the connection, for example, an unthreaded extension to either connecting member 100 or connecting member 200 of the connection.

Taking a partial sectional view along line A—A results in the depiction of the features in FIG. 2A. Nut portion 200 has a projection 203 on the root of a thread segment 202. Bolt 100 has a finger 103 projecting from an interrupted portion of a thread whose crest is 101 and root is 102. Arrow 301 shows the direction of relative movement of the nut component during assembly, while arrow 302 shows the direction of relative movement for the bolt component during assembly.

FIG. 2A depicts an important feature of the lead-in portion of the screw threads incorporating the latch of the present invention. The normal thread root 202 of the nut 200 is closer to the bolt 100 than the root in the lead-in area. The lead-in area root radius 205 is greater than root radius 202 by an amount 304. The function of this increased radius is to allow finger 103 to enter the thread form in its relaxed state, thereby having no impact on ease of initial assembly and preventing it from being inadvertently toggled forward during the process. Only when the threads are properly mated and threading begun will the projection 203 place the finger 103 into the correct orientation.

FIG. 2B shows the interaction of the fingers 103 and the projection 203 during assembly. Since the finger 103 is made of a relatively flexible material, and made thin enough to be quite flexible, finger 103 readily deflects to allow assembly.

FIG. 2C continues the assembly process as the two components are rotated into a tight connection. the feature has little or no impact on assembly at this stage. This figure also depicts another variable. Angle 305 is the angle between the finger 103 when in the assembled position and a line drawn from the center of the component 100 and a point at the center of the base of finger 103. This angle 305 determines a few crucial operating parameters of the device. Too shallow an angle 305—for example, less than 5 degrees—allows finger 103 to pass projection 203 with little interference, giving rise to the finger "skipping" over projection 203. On the other hand, too steep and angle 305, i.e., 75 degrees—may also allow the finger 103 to skip over the projection 203. Hence the device fails to function at too shallow or too steep an angle. At the operative range of angles, steeper angles correspond to longer fingers 103, and thus increased distortion required of part 200, as will be described below. Because distortion of part 200 is a primary determinant of unscrewing force, steeper angles of finger 103 also correspond to increased unscrewing force. Those skilled in the art will be able to easily determine angular orientation with little or no experimentation, taking into consideration the application at hand and the materials, composition and construction characteristics of the particular connection.

FIG. 2D depicts the start of the disassembly, as arrow 301 shows the direction of relative rotation of the nut and arrow 302 shows the direction of relative rotation of the bolt. Finger 103 comes into contact with projection 203. The reverse angle of finger 103 imparted during assembly now becomes an impediment to disassembly, jamming against projection 203.

FIG. 2E depicts the presence of sufficient force to begin to overcome the latching features. As rotational force is supplied in the direction of arrows 301 and 302, the straightening of finger 103 forces part 200 to deform outward in the direction of arrow 303. This allows the finger 103 to begin the "toggle over."

FIG. 2F depicts the continued disassembly after overcoming the latching feature. Finger 103 now leans in a direction which will no longer prevent disassembly. Nut 200 may now recover to its original circular cross-section.

Figure 2G:
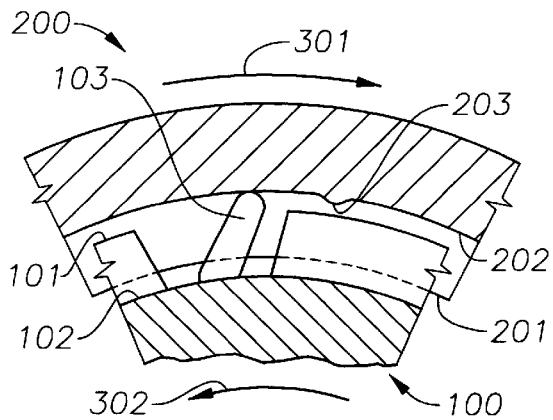
FIG. 2G is the same partial, sectional view of FIG. 2F except the feature of the present invention has been entirely overcome and no further resistance to disassembly will be created.

FIG. 2G depicts the feature after disassembly, with finger 103 no longer providing any material resistance to disassembly.

While depicted in a single material, two-component assembly, it is important to note that the latch can be incorporated using multiple materials in multiple components. Again with reference to FIG. 1, bolt 100 could be made of metal, and a slot could be machined into the side of the bolt. Fingers 103 could then be provided in the form of an inserted, flexible material such as plastic or spring steel.

Alternatively, if the connecting member 200 is made of metal, it would likely resist the deformation required to allow non-destructive passage of the fingers 103. Disassembly would likely require forces sufficient to shear the fingers 103 off the projection 120. In that case, if the fingers 103 were thin and somewhat flexible, this might not require too much force, although the sheared remnants of fingers 103 would indicate that the connection had been disassembled. From such considerations as material, finger 103 sizing, engagement angle 305 and projection 203 sizing, the device of the present invention provides enormous flexibility to designers.

Figure 3:
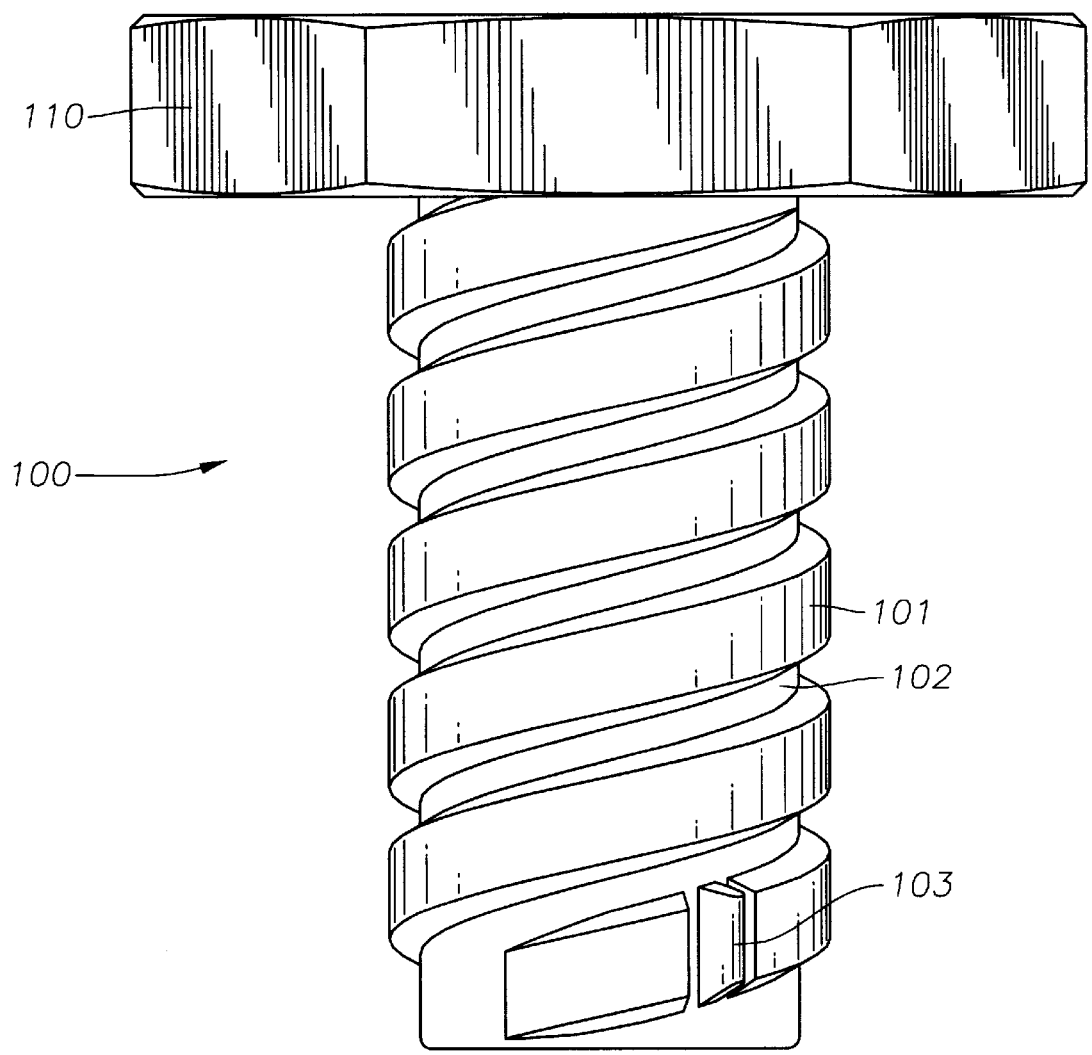
FIG. 3 is a view of an alternative preferred embodiment of the device of the present invention, showing the feature deployed merely as a stop to prevent the nut from being fully removed from the bolt.
Figure 3:
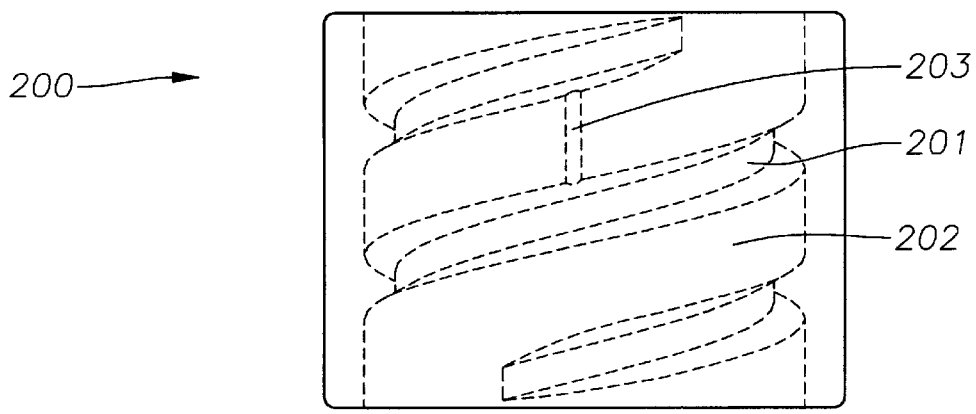
Figure 4:
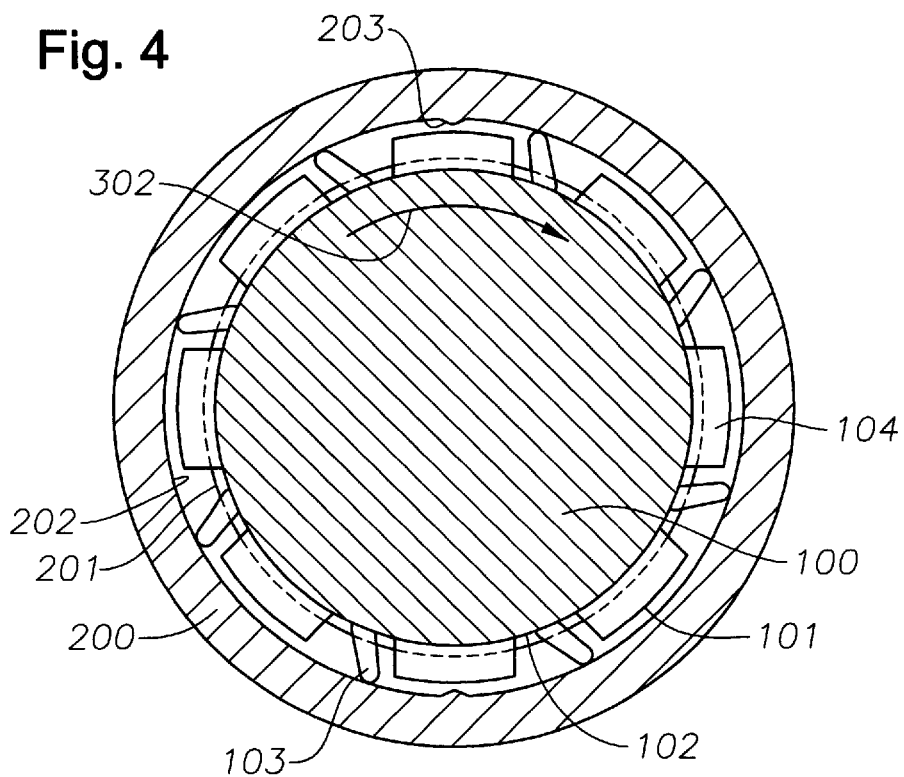
FIG. 4 is a sectional view of a device showing an alternate preferred embodiment of the device of the present invention. In this case, more than one set of interacting features is shown.

With reference to FIG. 3, the finger 103 is present only once, while projections 203 are present in plurality. In this embodiment, resistance to unscrewing is only present at the very end of the disassembly process. In this sense the feature provides a "nut retention" benefit, i.e., useful when complete disassembly and dropping the female component could be a problem (e.g. when a nut could fall into an engine or drop onto an operating electronic circuit board).

Since it is possible that component 200 may be threaded all the way down the shaft of the companion component 100, even past the point where the finger 103 is engaged within female component 200, this embodiment requires some special consideration. Since finger 103 is "cocked" in the correct direction to resist disassembly as the projection 203 in the component 200 passes it, it is important that finger 103 not re-straighten after it is completely out of the component 200. Hence, the finger 103 must be made of some deformable material, rather that the elastic fingers 103 in other embodiments.

Now with reference to the cross-sectional alternative preferred embodiment in FIG. 3, a multitude of fingers 103 are depicted along interrupted thread segments 104 with crests 101 and roots 102 on the component 100. The component 200 has two projections 203 emanating from the root section 202 of the threads. In the presence of rotational forces acting in the direction of the arrow 302, the fingers 103 pass easily over the projections 203. In effect the fingers 103 "ratchet" over the projections 203. Disassembly now requires substantial and continued application of rotational force in the opposite direction of the arrow 302. Accordingly, the component 200 could be readily placed anywhere along the threads of the part 100, yet require higher force levels to disassemble.

The choice of tool used to disassemble the connection has additional impact on the force required to complete the disassembly. If a rigid, metal cylinder (say a metal socket) is placed over the component 200, the metal cylinder would serve to reinforce the anti-rotation feature as it prevents the part 200 from distorting to allow the finger 103 to pass. Conversely, if a segmented metal cylinder is used to grip the component 200, disassembly might still be achieved at relatively low levels of force.

Figure 5:
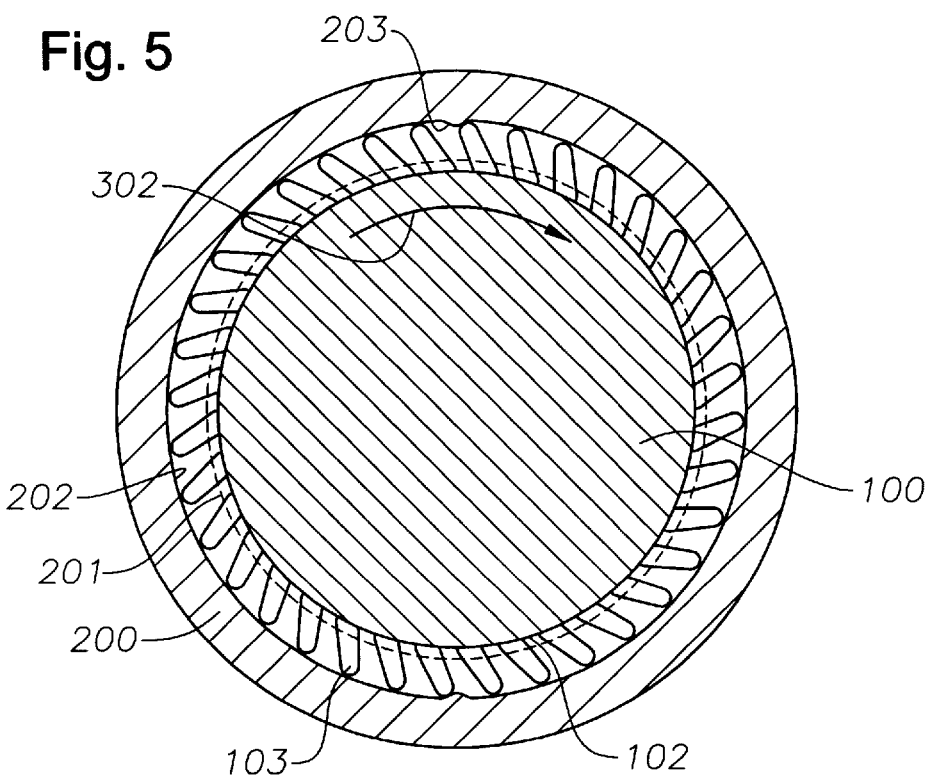
FIG. 5 is a sectional view of yet another preferred embodiment of the device of the present invention. In this case, the entire thread is replaced by locking features which now provide not only resistance to unscrewing but also all of the mechanical strength of the threads themselves.

Now with reference to the alternative preferred embodiment show in cross-sectional view FIG. 5, the proportion of fingers is increased to maximum. There are no thread segments left on connecting member 100. The multitude of fingers 103 now provides the mechanical strength normally associated with the threads themselves.

Figure 6:
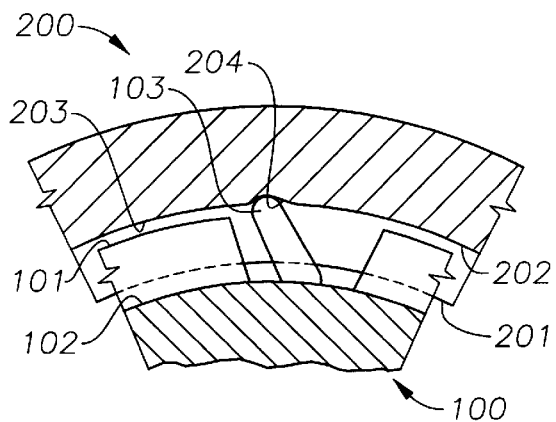
FIG. 6 is a partial sectional view of an alternative preferred embodiment of the device of the present invention. Rather than requiring projections on one side of the mating connection to interfere with a projection emanating from the other side, this view depicts the same result being achieved with a recess on one side of the connection.

Finally, with reference to the alternative preferred embodiment shown in the partial cross-sectional view of FIG. 6, the obstructions to passage to the finger 103 is provided not by projections but by a recess 204. This configuration may be easier to manufacture in metal, allowing standard threads to be cut and then a follow-on operation would create the recesses.

While all of the above embodiment depict the fingers on the male component and obstructions on the female, it may also be appreciated from FIG. 6 that there is no reason these two cannot be reversed and the same objectives achieved.

Figure 7:
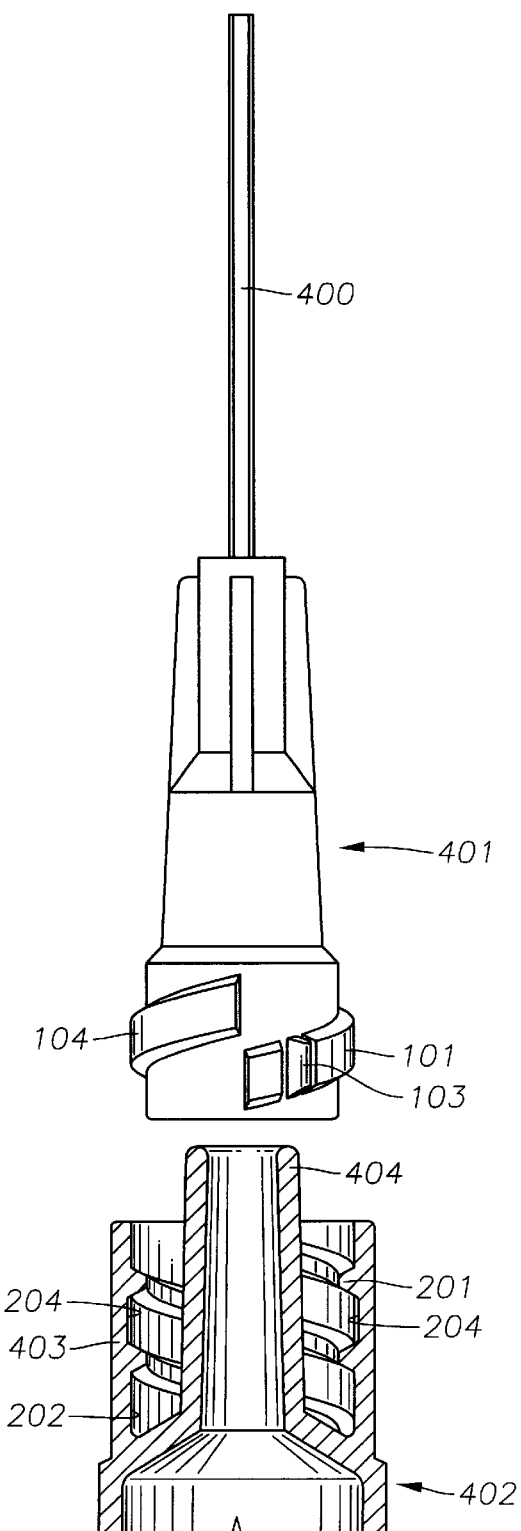
FIG. 7 is a partial view of an alternate preferred embodiment of the device including a syringe. The connection incorporated on a common medical fitting know as a "Luer," and would serve to keep the needle assembly from becoming disengaged from the barrel under high fluid pressures, axial loading or vibration.

Now with respect to FIG. 7, the device of the current invention is shown incorporated on a standard fitting (known in the industry as a "Luer") and a syringe. In this embodiment, the needle 400 is bonded in industry-standard fashion to a hub 401. The hub 401 incorporates a rigid thread segment 104 and a flexible finger 103. The rigid thread segments have crests 101, although there is no clear root area.

Mating is provided to a syringe barrel 402, shown in partial horizontal cross-section. The hub and barrel form housing members which include an area for receipt of a liquid, either to be injected into or withdrawn from a body, such as the arm of a human. The nozzle 404 fits inside the hub 401, and the hub threads 104 engage mating features on the threaded portion of the barrel (herein the "thread cage," 403). The thread cage 403 has threads with crest 201 and root 202. This thread cage 403 also has a recess 204 molded into a portion of a thread root 202. When mated securely, the finger 103 engages recess 204 preventing accidental disassembly, vibration-loosening, plastic-creep induced loosening and detachment under modest axial loading.

It can easily be appreciated from FIG. 7 that the locations of these features may be inverted—that is, the hub 401 may contain a recess 204 and the thread cage 403 may have the fingers 103. It may also be appreciated that projections from the root 202 on thread cage 403 may be substituted for recess 204.

Although the invention has been described in terms of specified embodiments which are set forth in detail, it should be understood that this is by illustration only and that the invention is not necessarily limited thereto, since alternative embodiments and operating techniques will be come apparent to those skilled in the art in view of the disclosure. Accordingly, modifications are contemplated which can be made without departing from the spirit of the described invention.

What is claimed and desired to be secured by Letters Patent is:

1. A syringe for introduction or withdrawal of a liquid from a body, said syringe comprising:
   (a) a hollow needle for penetrating said body;
   (b) a hub receiving said needle;
   (c) a syringe barrel selectively engageable to said hub for receipt of said liquid;
   (d) an exterior thread profile including first crest and root portions on one of said hub and said barrel;
   (e) an interior thread profile including second crest and root portions on the other of said hub and barrel;
   (f) at least one flexible finger extending outwardly from within one of the first and second root portions, said at least one flexible finger having a distal end normally projecting outwardly of said one of said first and second crests; and (g) at least one outwardly extending ridge portion on the other of said hub and said barrel, said ridge portion forming a part of the root of the thread profile of said other of said hub and barrel, whereby during thread engagement movements of said connecting members, said finger is flexed in one direction by said ridge portion and during threaded disengagement movements of said members, said finger is flexed in the opposite direction by said ridge for resistance to said disengagement movements.

2. The syringe of claim 1 wherein the root of the thread of said other of said hub and barrel is radially outwardly expanded on one side of said ridge and radially inwardly contracted on the other side of said ridge.

3. A syringe for introduction or withdrawal of a liquid from a body, said syringe comprising:

(a) a hollow needle for penetrating said bodies;

(b) a hub receiving said needle;

(c) a syringe barrel selectively engageable to said hub for receipt of said liquid, each of said hub and barrel including normally non-interfering interconnectable threaded profiles thereon;

(d) flexible projection means within the thread profile on one of said hub and said barrel; and (e) abutment means within the thread profile of the other of said hub and said barrel for interfering contact with said projection means, said projection and abutment means being oriented relative to one another whereby impediment to interconnecting manipulations between the thread profiles of said hub and said barrel in a first direction is avoided and thread disengagement is resisted between said members when said members are thereafter manipulated in a second direction.

4. A syringe for introduction or withdrawal of a liquid from a body, said syringe comprising:

(a) a housing including first and second housing members;

(b) a hollow needle extendable from said housing for penetrating said body;

(c) a retainer for said liquid within said housing;

(d) normally non-interfering interconnectable threaded profiles on each of said housing members;

(e) flexible projection means within the thread profile of one of said first and second housing members; and (f) abutment means within the thread profile of the other of said first and second housing members for interfering contact with said projection means, said projection and abutment means being oriented relative to one another where by impediment to threading interconnecting manipulations between the thread profiles of said members in a first direction is avoided and thread disengagement is resisted between said members when said members are thereafter manipulated in a second direction.

* * * * *